United States Patent [19]

Nyfeler

[11] Patent Number: 4,546,099
[45] Date of Patent: Oct. 8, 1985

[54] N-AMINOMETHYL-3-PHENYL-4-CYANOPYRROLE DERIVATIVES, COMPOSITIONS AND USE THEREOF AS MICROBICIDES

[75] Inventor: Robert Nyfeler, Basel, Switzerland

[73] Assignee: Ciba-Geigy Corporation, Ardsley, N.Y.

[21] Appl. No.: 632,168

[22] Filed: Jul. 18, 1984

[30] Foreign Application Priority Data

Jul. 22, 1983 [CH] Switzerland .......................... 4031/83

[51] Int. Cl.$^4$ .................... A01N 43/36; A01N 43/84; C07D 207/34; C07D 413/06
[52] U.S. Cl. .................................. 514/212; 514/222; 514/232; 514/237; 514/252; 514/290; 514/307; 514/314; 514/326; 514/427; 544/58.5; 544/60; 544/141; 544/372; 546/101; 546/145; 546/165; 546/208; 548/465; 548/524; 548/561; 260/245.7
[58] Field of Search ................ 544/58.5, 60, 141, 372; 546/101, 145, 165, 208; 548/465, 524, 561; 260/245.7; 424/248.52, 248.58, 248.4, 250, 256, 258, 267, 274

[56] References Cited

FOREIGN PATENT DOCUMENTS 2028363 12/1970 Fed. Rep. of Germany.
2927480 1/1980 Fed. Rep. of Germany.
2078761 1/1982 United Kingdom.

OTHER PUBLICATIONS

Van Leusen et al., "A New and Simple Synthesis of the Pyrrole Ring . . . ", Tetrahedron Letters 52, 5337-5340 (1972).

Primary Examiner—Robert W. Ramsuer
Attorney, Agent, or Firm—Edward McC. Roberts

[57] ABSTRACT

The invention relates to novel N-aminomethyl-3-phenyl-4-cyanopyrrole derivatives of the formula I

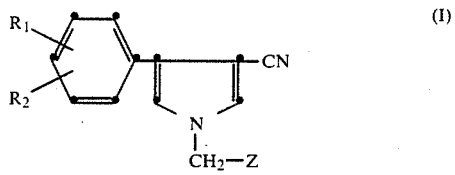

wherein
$R_1$ and $R_2$ are each independently hydrogen, halogen, methoxy or methylthio,
Z is a group

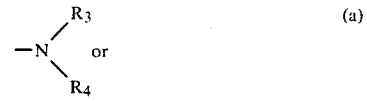

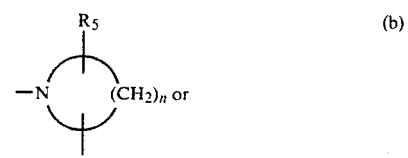

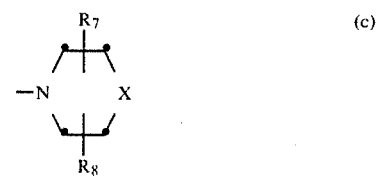

wherein
$R_3$ and $R_4$ are each independently hydrogen, $C_1$-$C_6$alkyl which is unsubstituted or substituted by cyano, $C_1$-$C_6$alkoxy or $C_1$-$C_6$alkoxycarbonyl; or are $C_3$-$C_6$alkenyl, $C_3$-$C_6$alkynyl, $C_3$-$C_7$cycloalkyl, benzyl or benzyl which is substituted by halogen, $C_1$-$C_6$alkyl, $C_1$-$C_6$haloalkyl and/or $C_1$-$C_6$alkoxy, or phenyl or phenyl which is substituted by halogen, $C_1$-$C_6$alkyl, $C_1$-$C_6$haloalkyl and/or $C_1$-$C_6$alkoxy, with the proviso that only one of $R_3$ or $R_4$ can be hydrogen,
$R_5$ and $R_6$ are each independently hydrogen, $C_1$-$C_6$alkyl, $C_1$-$C_6$alkoxycarbonyl, or both taken together form a fused aromatic ring,
n is 4 or 5,
X is oxygen, sulfur, $>C=O$ or $>N-R$,
$R_7$ and $R_8$ are each independently hydrogen, $C_1$-$C_6$alkyl or $C_1$-$C_6$alkoxycarbonyl, and
$R_9$ is hydrogen, $C_1$-$C_6$alkyl, formyl, $C_1$-$C_6$alkanoyl or $C_1$-$C_6$alkoxycarbonyl.

The invention further relates to the preparation of the compounds of formula I and to microbicidal compositions which contain at least one of said compounds. Also disclosed is a method of controlling phytopathogenic micro-organisms, which comprises the use of the novel compounds or compositions.

9 Claims, No Drawings

N-AMINOMETHYL-3-PHENYL-4-CYANOPYRROLE DERIVATIVES, COMPOSITIONS AND USE THEREOF AS MICROBICIDES

The present invention relates to novel N-aminomethyl-3-phenyl-4-cyanopyrrole derivatives of the formula I below, to the preparation thereof, and to microbicidal compositions which contain at least one of the title compounds. The invention also relates to the preparation of said compositions and to the use of the novel compounds and compositions for controlling harmful micro-organisms, in particular phytopathogenic fungi.

Specifically, the invention relates to compounds of the formula I

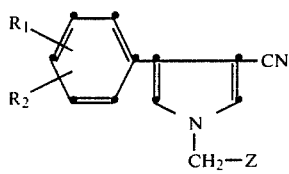

wherein
$R_1$ and $R_2$ are each independently hydrogen, halogen, methoxy or methylthio,
Z is a group

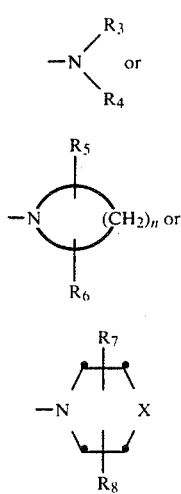

wherein
$R_3$ and $R_4$ are each independently hydrogen, $C_1-C_6$alkyl which is unsubstituted or substituted by cyano, $C_1-C_6$alkoxy or $C_1-C_6$alkoxycarbonyl; or are $C_3-C_6$alkenyl, $C_3-C_6$alkynyl, $C_3-C_7$cycloalkyl, benzyl or benzyl which is substituted by halogen, $C_1-C_6$alkyl, $C_1-C_6$haloalkyl and/or $C_1-C_6$alkoxy, or phenyl or phenyl which is substituted by halogen, $C_1-C_6$alkyl, $C_1-C_6$haloalkyl and/or $C_1-C_6$alkoxy, with the proviso that only one of $R_3$ or $R_4$ may be hydrogen,
$R_5$ and $R_6$ are each independently hydrogen, $C_1-C_6$alkyl, $C_1-C_6$alkoxycarbonyl, or both taken together form a fused aromatic ring,
n is 4 or 5,
X is oxygen, sulfur, $>C=O$ or $>N-R_9$
$R_7$ and $R_8$ are each independently hydrogen, $C_1-C_6$alkyl or $C_1-C_6$alkoxycarbonyl, and
$R_9$ is hydrogen, $C_1-C_6$alkyl, formyl, $C_1-C_6$alkanoyl or $C_1-C_6$alkoxycarbonyl.

Depending on the indicated number of carbon atoms, alkyl by itself or as moiety of another substituent comprises e.g. the following groups: methyl, ethyl, propyl, butyl, pentyl, hexyl etc., and the isomers thereof, e.g. isopropyl, isobutyl, tert-butyl, isopentyl etc. Haloalkyl denotes a mono- to perhalogenated alkyl substituent, e.g. $CH_2Cl$, $CHCl_2$, $CCl_3$, $CH_2Br$, $CHBr_2$, $CBr_3$, $CHF_2$, $CF_3$, $CCl_2F$, $CCl_2-CHCl_2$, $CH_2CH_2F$, $CI_3$ etc., with $CF_3$ being preferred. In formula I and throughout this specification, halogen denotes fluorine, chlorine, bromine or iodine, with fluorine, chlorine or bromine being preferred. Alkenyl is e.g. vinyl, 1-propenyl, allyl, 1-butenyl, 2-butenyl, 3-butenyl etc., as well as alkyl chains which are interrupted by several C=C double bonds. Alkynyl is e.g. 2-propynyl, propargyl, 1-butynyl, 2-butynyl etc., with propargyl being preferred. Depending on the indicated number of carbon atoms, cycloalkyl is e.g. cyclopropyl, cyclobutyl, cyclopentyl, cyclohexyl, cycloheptyl etc. Alkanoyl signifies a straight chain or branched alkyl group which is attached to a carbonyl group. If $R_5$ and $R_6$ together form a fused aromatic ring, Z is preferably a group

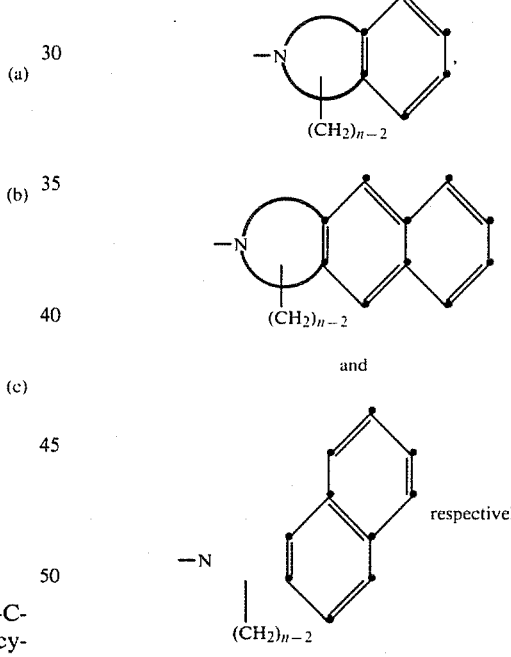

in which n is as defined for formula I.

The compounds of formula I are oils, resins or mainly crystalline solids which are stable under normal conditions and have extremely valuable microbicidal properties. They can be used in particular under field conditions in agriculture or related fields curvatively and, most particularly, preventively for controlling phytopathogenic micro-organisms. The compounds of formula I exhibit excellent fungicidal properties when applied in wide ranges of concentration and their use poses no problems.

In increasing order of preference, the following groups of compounds are preferred on account of their pronounced microbicidal activity:

(a) Compounds of the formula I, wherein $R_1$ and $R_2$ are each independently hydrogen, chlorine, methoxy or methylthio, Z is a group

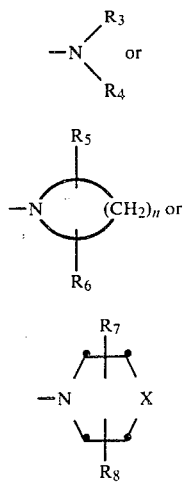

wherein $R_3$ and $R_4$ are each independently hydrogen, $C_1$-$C_6$alkyl, $C_1$-$C_3$alkyl which is substituted by cyano, $C_1$-$C_3$alkoxy or $C_1$-$C_3$alkoxycarbonyl; or are $C_3$-$C_4$alkenyl, $C_3$-$C_4$alkynyl, $C_5$-$C_6$cycloalkyl, benzyl or benzyl which is substituted by halogen, methyl, trifluoromethyl and/or methoxy, or phenyl or phenyl which is substituted by halogen, methyl, trifluoromethyl and/or methoxy, with the proviso that only one of $R_3$ or $R_4$ may be hydrogen; $R_5$ and $R_6$ are each independently hydrogen, $C_1$-$C_3$alkyl or $C_1$-$C_3$alkoxycarbonyl, or both taken together form a fused phenyl ring; n is 4 or 5, X is oxygen, sulfur, >C=O or >N-$R_9$; $R_7$ and $R_8$ are each independently hydrogen, $C_1$-$C_3$alkyl or $C_1$-$C_3$alkoxycarbonyl; and $R_9$ is hydrogen, $C_1$-$C_3$alkyl, formyl, $C_1$-$C_3$alkanoyl or $C_1$-$C_3$alkoxycarbonyl;

(b) Compounds of the formula I, wherein $R_1$ is in the 2-position and $R_2$ is in the 3-position and each independently of the other is hydrogen, chlorine, methoxy or methylthio; Z is a group

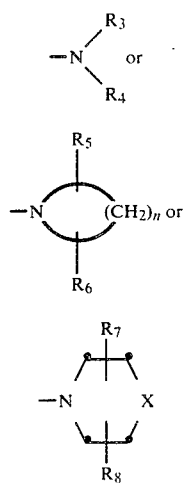

wherein $R_3$ and $R_4$ are each independently $C_1$-$C_6$alkyl, $C_1$-$C_2$alkyl which is substituted by cyano, $C_1$-$C_3$alkoxy or $C_1$-$C_3$alkoxycarbonyl; or are allyl, propargyl, cyclopentyl, cyclohexyl, benzyl, halobenzyl, phenyl or halophenyl; $R_5$ and $R_6$ are each independently hydrogen, methyl or $C_1$-$C_3$alkoxycarbonyl, or both taken together form a fused phenyl ring; n is 4 or 5, X is oxygen, sulfur, >C=O or >N-$R_9$ and $R_7$ and $R_8$ are each independently hydrogen, $C_1$-$C_2$alkyl, formyl, $C_1$-$C_3$alkanoyl or $C_1$-$C_3$alkoxycarbonyl;

(c) Compounds of the formula I, wherein $R_1$ is hydrogen or 2-chloro and $R_2$ is hydrogen or 3-chloro; Z is a group

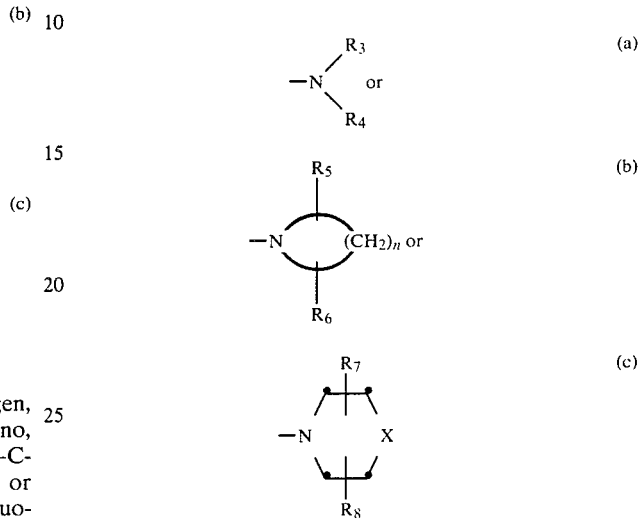

wherein $R_3$ and $R_4$ are each independently $C_1$-$C_6$alkyl, $C_1$-$C_2$alkyl which is substituted by cyano, $C_1$-$C_3$alkoxy or $C_1$-$C_3$alkoxycarbonyl; or are allyl, propargyl, cyclopentyl, cyclohexyl, benzyl, halobenzyl, phenyl or halophenyl; $R_5$ and $R_6$ are each independently hydrogen, methyl or $C_1$-$C_3$alkoxycarbonyl, or both taken together form a fused phenyl ring; n is 4 or 5, X is oxygen, sulfur, >C=O or >N-$R_9$ and $R_7$ and $R_8$ are each independently hydrogen, $C_1$-$C_2$alkyl, formyl, $C_1$-$C_3$alkanoyl or $C_1$-$C_3$alkoxycarbonyl.

Examples of particularly preferred individual compounds are:

N-(N',N'-dimethylaminomethyl)-3-(2,3-dichlorophenyl)-4-cyanopyrrole (compound 1.1), N-(N'-benzyl-N'-methylaminomethyl)-3-(2,3-dichlorophenyl)-4-cyanopyrrole (compound 1.9), N-[N'-methyl-N'-(2-cyanoethyl)aminomethyl]-3-(2,3-dichlorophenyl)-4-cyanopyrrole (compound 1.16), N-[N'-isopropyl-N'-(2-cyanoethyl)aminomethyl]-3-(2,3-dichlorophenyl)-4-cyanopyrrole (compound 1.23), N-(piperidin-1-ylmethyl)-3-(2,3-dichlorophenyl)-4-cyanopyrrole (compound 1.45), N-(3-ethoxycarbonylpiperidine-1-ylmethyl)-3-(2-chlorophenyl)-4-cyanopyrrole (compound 1.48), N-(morpholin-1-ylmethyl)-3-(2,3-dichlorophenyl)-4-cyanopyrrole (compound 1.55), N-(2,6-dimethylmorpholin-1-ylmethyl)-3-(2-chlorophenyl)-4-cyanopyrrole (compound 1.61), N-[N'-cyclopentyl-N'-(2-cyanoethyl)aminomethyl]-3-(2,3-dichlorophenyl)-4-cyanopyrrole (compound 1.29), N-(2,6-dimethylmorpholin-1-ylmethyl)-3-(2,3-dichlorophenyl)-4-cyanopyrrole (compound 1.63/1.75), N-(4-acetylcarbonylpiperazin-1-ylmethyl)-3-(2,3-dichlorophenyl)-4-cyanopyrrole (compound 1.68), N-[N'-2-(methoxyethyl)-N'-(2-cyanoethyl)aminomethyl]-3-(2,3-dichlorophenyl)-4-cyanopyrrole (compound 1.34),
N-[N'-methyl-N'-(2-cyanoethyl)aminomethyl]-3-(2-chlorophenyl)-4-cyanopyrrole (compound 1.11),
N-[N'-methyl-N'-(2-methoxyethyl)aminomethyl]-3-(2,3-dichlorophenyl)-4-cyanopyrrole (compound 1.14),
N-[N'-(n-propyl)-N'-(2-cyanoethyl)aminomethyl]-3-(2,3-dichlorophenyl)-4-cyanopyrrole (compound 120),
N-[N'-(n-butyl)-N'-(2-cyanoethyl)aminomethyl]-3-(2,3-dichlorophenyl)-4-cyanopyrrole (compound 1.21),
N-[N'-methyl-N'-prop-2-enyl-aminomethyl]-3-(2,3-dichlorophenyl)-4-cyanopyrrole (compound 1.70),
N-[N'-propargyl-N'-cyclohexylaminomethyl]-3-(2,3-dichlorophenyl)-4-cyanopyrrole (compound 1.72).

The compounds of the formula I are prepared as follows:

(A) by reacting a compound of the formula II

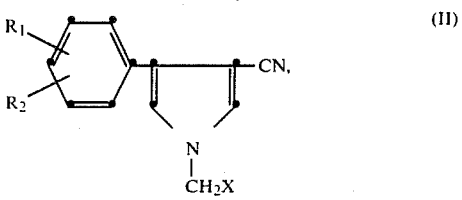

wherein $R_1$ and $R_2$ are as defined for formula I and X is OH or halogen, preferably chlorine, with a compound of the formula III

H-Z    (III)

wherein Z is as defined for formula I, in the presence of a base and optionally of a catalyst, in the temperature range from 0° to 100° C., preferably from 20° to 60° C.; or (B) by reacting a compound of the formula IV

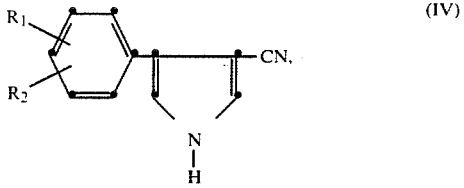

wherein $R_1$ and $R_2$ are as defined for formula I, either with formaldehyde and a compound of the formula III, in a protic solvent in the temperature range from 0° to 120° C., preferably from 20° C. to reflux temperature, in the presence of a basic or acid catalyst, or with 1,3,5-trioxane or paraformaldehyde and a compound of the formula III, in an aprotic solvent in the presence of a basic catalyst and in the temperature range from 0° to 120° C., preferably from 20° to 80° C.

Variant (A) (the reaction of II with III) is carried out in the absence or preferably in the presence of an inert solvent or mixture of solvents. Examples of such solvents are: aromatic and aliphatic hydrocarbons such as benzene, toluene, xylenes, petroleum ether, ligroin or cyclohexane; halogenated hydrocarbons such as chlorobenzene, methylene chloride, ethylene chloride, chloroform, carbon tetrachloride or tetrachloroethylene; ethers and ethereal compounds such a diethyl ether, diisopropyl ether, tert-butylmethyl ether, dimethoxyethane, dioxan, tetrahydrofuran or anisole; esters such as ethyl acetate, propyl acetate or butyl acetate; nitriles such as acetonitrile; or compounds such as dimethylsulfoxide, dimethylformamide, and mixtures of such solvents with one another.

The reaction rate can be speeded up in some cases by adding a catalyst, e.g. KI. An equimolar amount of base is normally added in this variant (A). Examples of suitable bases are organic bases such as trialkylamines (triethylamine, triethylamine etc.), pyridine and pyridine bases; or organic bases such as bicarbonates or carbonates of alkali metals and alkaline earth metals. In general, an excess of amine of the formula III can also be added as base.

Reaction variant (B) (reaction of III with IV) is preferably carried out in a suitable inert solvent. Examples of suitable protic solvents are: water, alcohols (preferably alkanols such as methanol, ethanol, isopropanol, n-propanol etc.), or carboxylic acids (preferably alkanecarboxylic acids such as formic acid, acetic acid, propionic acid etc.). If the process is carried out in a protic solvent, then the following reaction catalysts can, for example, be used: organic bases such as 1,8-diazabicyclo[5.4.0]undec-7-ene, tertiary amines such as trialkylamines (trimethylamine, triethylamine, dimethylethylamine etc.), triethylenediamine, piperidine, pyridine, 4-dimethylaminopyridine, 4-pyrrolidylpyridine etc., or inorganic bases such as the oxides, hydroxides, hydrides, carbonates, bicarbonates and alcoholates of alkali metals or alkaline earth metals (e.g. $Na_2CO_3$, $BaCO_3$, $MgCO_3$, $K_2CO_3$, $NaHCO_3$, $KHCO_3$, $Ca(HCO_3)_2$, $NaOCH_3$, $NaOC_2H_5$, $KO(iso-C_3H_7)$, $KO(tert$-butyl), NaH, CaO etc.); organic acids such as carboxylic acids (acetic acid, formic acid, propionic acid etc.), aliphatic and aromatic sulfonic acids such as methanesulfonic acid, ethanesulfonic acid, toluenesulfonic acid, benzenesulfonic acid etc.; inorganic acids such as mineral acids, e.g. phosphoric acid, sulfuric acid or hydrohalic acids (hydrochloric acid, hydrobromic acid, hydriodic acid or hydrofluoric acid). It is convenient to use catalytic amounts of acids or bases in this variant. In general, an excess of amine of the formula III will suffice. In this variant the formaldehyde is preferably used in the form of its aqueous solution (formaline) or as trimer (1,3,5-trioxane) or polymer (paraformaldehyde).

If the process of variant (B) is carried out in an aprotic solvent, then suitable solvents are e.g.: aliphatic or aromatic hydrocarbons such as benzene, toluene, a xylene, petroleum ether, ligroin or cyclohexane; ethers and ethereal compounds such as diethyl ether, diisopropyl ether, tert-butyl methyl ether, dimethoxyethane, tetrahydrofuran, dioxan or anisole; esters such as ethyl acetate, propyl acetate or butyl acetate, or compounds such as dimethylformamide, dimethylsulfoxide, or mixtures of such solvents with one another. The catalysts employed are e.g. the bases referred to above in the description of variant (A). In this variant it is preferred to use the formaldehyde in the form of 1,3,5-trioxane or paraformaldehyde. In both variants A and B the reaction is carried out with 1.0 to 1.5 equivalents of formaldehyde.

Amines of the formula III are known or they can be obtained by methods which are known per se.

The starting materials of the formula II can be obtained from the corresponding 3-phenyl-4-cyanopyrroles of the formula IV, for example by converting a compound of the formula IV by reaction with formaldehyde into the corresponding N-hydroxymethyl derivative of the formula V

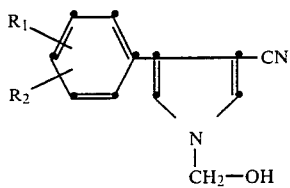

wherein $R_1$ and $R_2$ are as defined for formula I, and, if necessary, replacing the free OH group in V, in conventional manner, by a halogen, for example with thionyl chloride or phosphoroxy chloride.

The process for the preparation of compounds of the formula V is normally carried out in the temperature range from 0° to 200° C., preferably from 0° to 160° C., in a conventional inert organic solvent or mixture of solvents.

Some of the pyrroles of formula IV are known from the literature. Thus, for example, the method of preparing 4-cyano-3-phenylpyrrole and the chemical properties thereof are described in Tetrahedron Letters No. 52, pp. 5337–5340 (1972). No mention is made of the biological properties of the compound. Other representatives of formula IV can be prepared by methods similar to those employed for obtaining the known compounds.

Differently substituted 3-phenyl-4-cyanopyrrole derivatives are known from the literature. For example, pyrroles of the formula VI

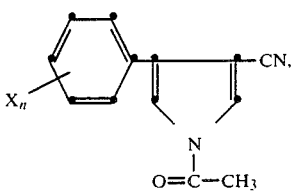

wherein X is a halogen atom, a lower alkyl group or lower haloalkyl group, and n is 0, 1 or 2, are described in DE-OS No. 2 927 480 and intermediates with limited fungicidal properties.

Pyrrole derivatives of the formula VII

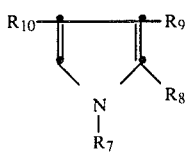

wherein
 $R_7$=acyl, alkoxycarbonylaklyl . . .
 $R_8$, $R_9$=H, aryl . . .
 $R_{10}$=hydroxy, mercapto
are known as heat and light stabilisers for PVC plastics from GB patent 2 078 761.

Further pyrrole derivatives of the formula VIII

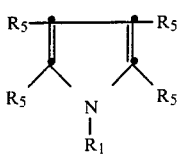

wherein
 $R_1$=alkyl, unsubstituted or substituted by acyloxy . .

$R_5$=H, alkyl, CN . . .
are known as polymerisation catalysts for vinyl chloride from DE-OS No. 2 028 363.

The known pyrrole derivatives are either inactive to phytopathogens or in the greenhouse they have a marked fungicidal activity which is not reproduced under field conditions owing to their instability to environmental influences. They are therefore not suitable for practical application in agriculture, in horticulture or in related fields of use. In contradistinction thereto, the novel pyrrole derivatives of the formula I constitute a useful enlargement of the art, for it has surprisingly been found that they have, for practical field application purposes, a very advantageous microbicidal activity spectrum against phytopathogenic fungi and bacteria. They can be used not only in crop growing or similar fields of use for controlling harmful micro-organisms in cultivated plants, but additionally in storage protection for preserving perishable goods. Compounds of formula I have very advantageous curative, systemic and, in particular, preventive properties, and can be used for protecting numerous cultivated plants, in particular field crops. With the compounds of formula I it is possible to inhibit or destroy the micro-organisms which occur in plants or in parts of plants (fruit, blossoms, leaves, stems, tubers, roots) in different crops of useful plants, while at the same time the parts of plants which grow later are also protected from attack by such micro-organisms.

The compounds of formula I are effective for example against the phytopathogenic fungi belonging to the following classes: Ascomycetes, e.g. Erysiphe, Sclerotinia, Fusarium, Monilinia, Helminthosporium; Basidiomycetes, e.g. Puccinia, Tilletia, Rhizoctonia; as well as the Oomycetes belonging to the class of Phycomycetes, e.g. Phytophthora. As plant protective agents, the compounds of formula I can be used with particular success against important noxious fungi of the Fungi imperfecti family, e.g. against Cercospora, Piricularia and, in particular, against Botrytis. Botrytis spp. (*B. cinerea, B. allii*) and the grey mould on vines, strawberries, apples, onions and other varieties of fruit and vegetables is a noxious fungus that causes considerable economic damage. Furthermore, some compounds of the formula I can be successfully used for protecting perishable goods of vegetable or animal origin. They control mould fungi such as Penicillium, Aspergillus, Rhizopus, Fusarium, Helminthosporium, Nigrospora and Alternaria, as well as bacteria such as butyric acid bacteria and yeast fungi such as Candida.

As plant protective agents, the compounds of formula I have a very advantageous activity spectrum for practical application in agriculture for protecting cultivated plants, without damaging said plants by harmful side-effects. They can also be used as seed dressing agents for protecting seeds (fruit, tubers, grains) and plant cuttings against fungus infections and against phytopathogenic fungi which occur in the soil.

Accordingly, the invention also relates to microbicidal compositions and to the use of the compounds of formula I for controlling phytopathogenic microorganisms, in particular phytopathogenic fungi, and for the preventive treatment of plants and stored goods of vegetable or animal origin to protect them from attack by such micro-organisms.

The present invention also relates to the preparation of agrochemical compositions, which comprises homogeneously mixing the active ingredient (compound of formula I) with one or more substances or groups of substances described herein. The invention further relates to a method of treating plants or storable goods, which comprises applying the compounds of formula I or the novel compositions to said plants, parts of plants or to the locus thereof, or to the substrate.

Target crops to be protected within the scope of the present invention comprise e.g. the following species of plants: cereals (wheat, barley, rye, oats, rice, sorghum and related crops), beet (sugar beet and fodder beet), drupes, pomes and soft fruit (apples, pears, plums, peaches, almonds, cherries, strawberries, rasberries and blackberries), leguminous plants (beans, lentils, peas, soybeans), oil plants (rape, mustard, poppy, olives, sunflowers, coconut, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocasdos, cinnamon, camphor), or plants such as maize, tobacco, nuts, coffee, sugar cane, tea, vines, hops, bananas and natural rubber plants, as well as ornamentals (composites).

For storage protection, the compounds of formula I are used in unmodified form or, preferably, together with the adjuvants conventionally employed in the art of formulation, and are therefore formulated in known manner to e.g. emulsifiable concentrates, brushable pastes, directly sprayable or dilutable solutions, dilute emulsions, wettable powders, soluble powders, dusts, granulates, and also encapsulations in e.g. polymer substances. The methods of application, such as spraying, atomising, dusting, scattering or pouring, and the formulation of the composition, are chosen in accordance with the intended objectives and the prevailing circumstances. Suitable rates of application are in general in the range from 0.01 to not more than 2 kg of active ingredient per 100 kg of substrate to be protected. However, they depend very materially on the nature (surface area, consistency, moisture content) of the substrate and its environmental influences.

Within the scope of this invention, storable goods will be understood as meaning natural substances of vegetable and/or animal origin and the products obtained therefrom by further processing, for example the plants listed below whose natural life cycle has been interrupted and the parts thereof (stalks, leaves, tubers, seeds, fruit, grains) which are in freshly harvested or further processed form (predried, moistened, crushed, ground, roasted). The following produce may be cited by way of example, without any restriction to the field of use within the scope of this invention: cereals (wheat, barley, rye, oats, rice, sorghum and related crops); beet (carrots, sugar beet and fodder beet); drupes, pomes and soft fruit (apples, pears, plums, peaches, almonds, cherries, strawberries, rasberries and blackberries); leguminous plants (beans, lentils, peas, soybeans); oil plants (rape, mustard, poppy, olives, sunflowers, coconuts, castor oil plants, cocoa beans, groundnuts); cucumber plants (cucumber, marrows, melons); fibre plants (cotton, flax, hemp, jute, ramie); citrus fruit; vegetables (spinach, lettuce, asparagus, cabbages, carrots, anions, tomatoes, potatoes, paprika); lauraceae (avocados, cinnamon, camphor), or maize, tobacco, nuts, coffee, sugar cane, tea, vines, chestnuts, hops, bananas, grass and hay.

Examples of natural products of animal origin are, in particular, dried meat and processed fish products such as dry-cured meat, dry-cured fish, meat extracts, bone meal, fish meal and animal dry feeds.

The storable goods treated with compounds of the formula I are given lasting protection from attack by mould fungi and other harmful microorganisms. The formation of toxic and in some cases carcinogenic mould fungi (aflatoxins and ochratoxins) is inhibited, the goods are preserved from deterioration, and their quality is maintained over a prolonged period of time. The method of the invention is susceptible of application to all forms of dry and moist storable goods which are susceptible to attack by microorganisms such as yeast fungi, bacteria and, in particular, mould fungi.

A preferred method of applying active ingredient comprises spraying or wetting the substrate with a liquid formulation, or mixing the substrate with a solid formulation, of the active ingredient. The invention also relates to the described method of preserving storable goods.

The compounds of formula I are normally applied in the form of compositions and can be applied to the crop area, plant or substrate to be treated, simultaneously or in succession, with further compounds. These compounds can be both fertilisers or micronutrient donors or other preparations that influence plant growth. They can also be selective herbicides, insecticides, fungicides, bactericides, nematicides, mollusicides or mixtures of several of these preparations, if desired together with further carriers, surfactants or application promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a compound of the formula I, or an agrochemical composition which contains at least one of said compounds, is foliar application. The number of applications and the rate of application depend on the risk of infestation by the corresponding pathogen (species of fungus). However, the compound of formula I can also penetrate the plant through the roots via the soil (systemic action) by impregnating the locus of the plant with a liquid composition, or by applying the compounds in solid form to the soil, e.g. in granular form (soil application). The compounds of formula I may also be applied to seeds (coating) by impregnating the seeds either with a liquid formulation containing a compound of the formula I, or coating them with a solid formulation. In special cases, further types of application are also possible, e.g. selective treatment of the plant stems or buds.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha.

The formulations, i.e. the compositions, preparations or mixtures containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials or inorganic or organic nature can be used, e.g. especially dolomite or pulverised plant residues. Particularly advantageous application promoting adjuvants which are able to reduce substantially the rate of application are also natural (animal or vegetable) or synthetic phospholipids of the series of the cephalins and lecithins, e.g. phosphatidyl ethanolamine, phosphatidyl serine, phosphatidyl choline, sphingomyeline, phosphatidyl inisotol, phosphatidyl glycerol, lysolecithin, plasmalogenes or cardiolipin, which can be obtained e.g. from animal or plant cells, in particular from the brain, heart, liver, egg yokes or soya beans. Examples of useful physical forms are phosphatidyl choline mixtures. Examples of synthetic phospholipids are dioctanoylphosphatidyl choline and dipalmitoylphosphatidyl choline.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$ alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide. In the field of storage protection, the auxiliaries which are acceptable for human and animal nutrition are preferred.

The surfactants customarily employed in the art of formulation are described e.g. in "McCutcheon's Detergents and Emulsifiers Annual", MC Publishing Corp. Ridgewood, N.J., 1981; Helmut Stache "Tensid-Taschenbuch" (Tenside Handbook) Carl Hanser Verlag, Munich/Vienna, 1981.

The agrochemical compositions usually contain 0.1 to 99%, preferably 0.1 to 95%, of a compound of the formula I, 99.9 to 1%, preferably 99.8 to 5%, of a solid or liquid adjuvant, and 0 to 25%, preferably 0.1 to 25%, of a surfactant.

Whereas commercial products will preferably be formulated as concentrates, the end user will normally employ dilute formulations.

The compositions may also contain further auxiliaries such as stabilisers, antifoams, viscosity regulators, binders, tackifiers as well as fertilisers or other active ingredients for obtaining special effects.

Such agrochemical compositions also constitute an object of the present invention.

The invention is illustrated in more detail by the following Examples, without implying any restriction to what is described therein. Parts and percentages are by weight.

PREPARATORY EXAMPLES (a) Preparation of the starting materials

EXAMPLE S1

Preparation of

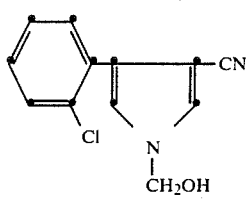
(compound 1)

N-Hydroxymethyl-3-(2-chlorophenyl)-4-cyanopyrrole 60.8 g of 3-(2-chlorophenyl)-4-cyanopyrrole, 9.9 g of paraformaldehyde and 0.8 g of triethylamine are thoroughly mixed and and the mixture is then heated, with stirring, at a bath temperature of 90° C. The resultant melt is cooled to room temperature after 1¼ hours, when it congeals to a glass-like solid. Recrystallisation from toluene yields the title compound in the form of brownish crystals of m.p. 94°–97° C.

The following compounds of the formula

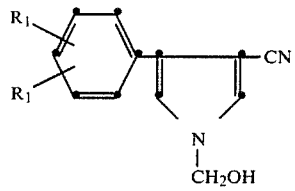

are prepared in analogous manner:

| Compound | R$_1$ | R$_2$ | m.p. [°C.] |
|---|---|---|---|
| 1 | 2-Cl | H | 94–97 |
| 2 | H | 3-Cl | 72–74 |
| 3 | 2-Cl | 3-Cl | 137–140 |
| 4 | 2-OCH$_3$ | H | viscous substance |
| 5 | H | H | 81–84 |
| 6 | 2-SCH$_3$ | H | resin |

EXAMPLE S2

Preparation of

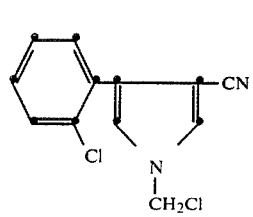
(compound 7)

N-Chloromethyl-3-(2-chlorophenyl)-4-cyanopyrrole

With efficient stirring, 48 g of N-hydroxymethyl-3-(2-chlorophenyl)-4-cyanopyrrole are added in several portions to 60 ml of thionyl chloride such that moderate gas evolution is maintained. When the evolution of gas ceases, the mixture is stirred for 2 hours at room temperature and then for 2½ hours at 35°–40° C. After cooling to room temperature, toluene is added and the mixture is concentrated. The residue is recrystallised from diethyl ether/petroleum, affording the title compound in the form of beige crystals with a melting point of 97°–99° C.

EXAMPLE S3

Preparation of

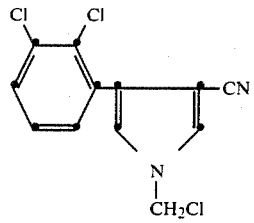
(compound 9)

N-Chloromethyl-3-(2,3-dichlorophenyl)-4-cyanopyrrole

To a solution of 23.7 g of 3-(2,3-dichlorophenyl)-4-cyanopyrrole in 300 ml of tetrahydrofuran are added 7.5 g of paraformaldehyde and then 1.5 ml of 1,8-diazabicyclo[5.4.0]undec-7-ene. The mixture is stirred for 3 hours at room temperature. With stirring, 21.7 ml of thionyl chloride are added dropwise at 20°–30° C. to the resultant hydroxymethyl derivative. The reaction mixture is stirred for 16 hours at room temperature, then poured into ice-water and extracted twice with ethyl acetate. The combined organic extracts are washed twice with a halogen-containing solution of sodium chloride, dried over sodium sulfate and filtered. The filtrate is concentrated and the residue is crystallised from ether/petroleum ether to give the title compound in the form of beige crystals with a melting point of 132°–133° C.

The following compounds of the formula

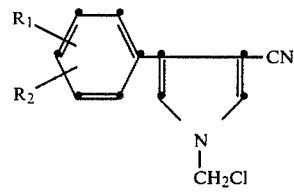

are also prepared in analogous manner:

| Compound | R₁ | R₂ | m.p. [°C.] |
| --- | --- | --- | --- |
| 7 | 2-Cl | H | 97–99 |
| 8 | H | 3-Cl | 77–79 |
| 9 | 2-Cl | 3-Cl | 132–133 |
| 10 | 2-OCH₃ | H | |
| 11 | H | H | |
| 12 | 2-SCH₃ | H | |

(β) Preparation of the final products

EXAMPLE P1

Preparation of (compound 1.61)

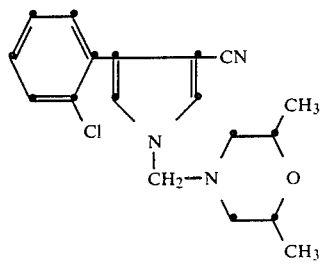

N-(2,6-Dimethylmorpholin-4-ylmethyl)-3-(2-chlorophenyl)-4-cyanopyrrole 10 g of N-chloromethyl-3-(2-chlorophenyl)-4-cyanopyrrole, 12.5 ml of 2,6-dimethylmorpholine (mixture of cis/trans isomers) and 0.1 g of potassium iodide are stirred in 200 ml of tetrahydrofuran for 16 hours at room temperature. The reaction mixture is poured into ice-water and extracted twice with ethyl acetate. The organic phase is washed twice with a semisaturated solution of sodium chloride, dried over sodium sulfate and filtered. The filtrate is concentrated and the residue is purified by chromatography over silica gel with a 2:3 mixture of ethyl acetate/petroleum ether as eluant. Subsequent crystallisation from ether/petroleum ether yields 6.8 g of compound 1.61 as a mixture of cis/trans isomers with a melting point of 120°–131° C.

EXAMPLE P2

Preparation of (compound 1.63/1.75)

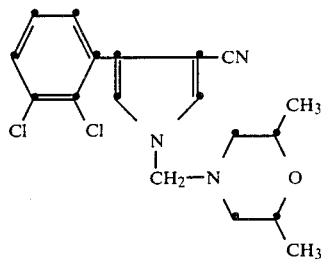

N-(2,6-Dimethylmorpholin-4-ylmethyl)-3-(2,3-dichlorophenyl)-4-cyanopyrrole

To a suspension of 10 g of 3-(2,3-dichlorophenyl)-4-cyanopyrrole in 35 ml of ethanol are added 5 ml of a 38% aqueous solution of formaldehyde and 0.4 ml of acetic acid. With stirring, 8.3 ml of 2,6-dimethylmorpholine (mixture of cis/trans isomers) are added dropwise, the temperature rising to 37° C. Then 14 ml of water are added dropwise and the solution is left to stand overnight at room temperature. Water is again added until the onset of turbidity. The batch is then cooled in an ice bath and the product begins to crystallise. The crystals are isolated by filtration and dried over phosphorus pentoxide, affording 8.5 g of brown crystals of the desired product as a mixture of cis/trans isomers. Melting point: 91°–97° C. The mother liquor is concentrated to a small volume and the residue is extracted with ethyl acetate and water. The organic phase is separated, washed twice with a semisaturated solution of sodium chloride, dried over sodium sulfate and concentrated. The residue is recrystallised from ether/petroleum ether, affording 0.8 g of a homogeneous diastereoisomer of the above product in the form of colourless crystals. Melting point: 102°–104° C.

EXAMPLE P3

Preparation of (Verb. Nr. 1.1)

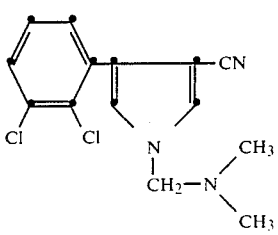

N-(N',N'-Dimethylaminomethyl)-3-(2,3-dichlorophenyl)-4-cyanopyrrole 5.9 g of 3-(2,3-dichlorophenyl)-4-cyanopyrrole are suspended in 30 ml of ethanol and to the suspension are added 2.4 ml of a 38% aqueous solution of formaldehyde and then 3.3 ml of a 41.6% aqueous solution of dimethylamine. The ensuing reaction is weakly exothermic and a clear solution forms. Spontaneous crystallisation commences after 16 hours at room temperature. The batch is stood in a cooling cabinet for 2 hours and then the beige crystals are isolated by filtration and dried, affording 6.3 g of the title compound of m.p. 128°–130° C.

EXAMPLE P4

Preparation of (compound 1.23)

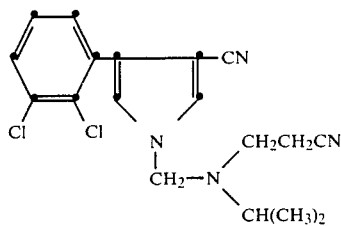

N-[N'-Isopropyl-N'-(2-cyanoethyl)aminomethyl]-3-(2,3-dichlorophenyl)-4-cyanopyrrole To a suspension of 2.8 g of 2-(2,3-dichlorophenyl)-4-cyanopyrrole in 12 ml of ethanol are added 1 ml of a 38% aqueous solution of formaldehyde and then 1.5 ml of 3-isopropylaminopropionitrile. The reaction mixture is then heated under reflux until a clear solution is obtained. Crystals gradually precipitate as the solution cools. The reaction mixture is then allowed to stand for 6 hours at room temperature and then for 14 hours at 7° C. The colourless crystals are then isolated by filtration and dried, affording 3 g of the title compound of m.p. 104°–106° C.

EXAMPLE P5

Preparation of

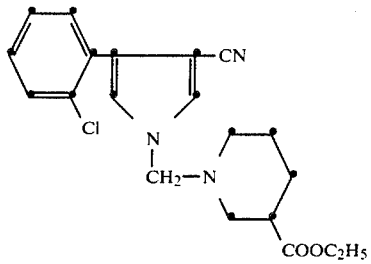

(compound Nr. 1.48)

N-(3-Ethoxycarbonylpiperazin-1-ylmethyl)-3-(2-chlorophenyl)-4-cyanopyrrole 4.9 g of 3-(2-chlorophenyl)-4-cyanopyrrole are dissolved in 50 ml of anhydrous tetrahydrofuran and to this solution are added 0.4 ml of diazabicyclo[5.4.0]undec-7-ene. The mixture is stirred overnight and the resulting clear solution is concentrated. The residue is purified by chromatography over silica gel with ethyl acetate/petroleum ether as eluant, affording the title compound as a yellow resin.

$n_D^{50} = 1.5571$.

The following compounds of formula I are also prepared in accordance with the procedures described in the foregoing Examples:

TABLE 1

Compound of the formula

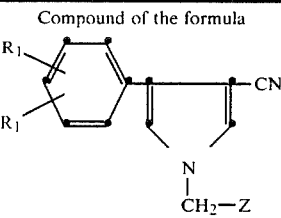

| Compound | $R_1$ | $R_2$ | Z | Physical data [°C.] |
|---|---|---|---|---|
| 1.1 | 2-Cl | 3-Cl | —N(CH₃)₂ | m.p. 128–130° |
| 1.2 | H | H | —N(CH₃)₂ | m.p. 72–75° |
| 1.3 | 2-Cl | H | —N(CH₃)₂ | m.p. 92–96° |
| 1.4 | H | 3-Cl | —N(CH₃)(C₄H₉(n)) | |
| 1.5 | 2-OCH₃ | H | —N(CH₃)(C₄H₉(n)) | |
| 1.6 | 2-Cl | 3-Cl | —N(CH₃)(C₄H₉(n)) | |

TABLE 1-continued

Compound of the formula

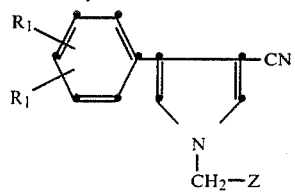

| Compound | $R_1$ | $R_2$ | Z | Physical data [°C.] |
|---|---|---|---|---|
| 1.7 | 2-SCH₃ | H | —N(C₆H₁₃(n))₂ | |
| 1.8 | H | H | —N(C₆H₁₃(n))₂ | |
| 1.9 | 2-Cl | 3-Cl | —N(CH₃)(CH₂-C₆H₅) | m.p. 73–78° |
| 1.10 | H | H | —N(CH₃)(CH₂-C₆H₅) | |
| 1.11 | 2-Cl | H | —N(CH₃)(CH₂-C₆H₄-Cl) | semi-crystalline |
| 1.12 | 2-Cl | 3-Cl | —N(CH₃)(C₆H₁₁) | |
| 1.13 | 2-Cl | H | —N(CH₃)(CH₂CH₂OCH₃) | |
| 1.14 | 2-Cl | 3-Cl | —N(CH₃)(CH₂CH₂OCH₃) | resin |
| 1.15 | H | H | —N(CH₃)(CH₂CH₂—CN) | m.p. 49–50° |
| 1.16 | 2-Cl | 3-Cl | —N(CH₃)(CH₂CH₂—CN) | m.p. 105–107° |
| 1.17 | H | 3-Cl | —N(CH₂CH₃)(CH₂CH₂—CN) | |
| 1.18 | 2-SCH₃ | H | —N(CH₂CH₃)(CH₂CH₂—CN) | |

TABLE 1-continued

Compound of the formula

| Compound | R₁ | R₂ | Z | Physical data [°C.] |
|---|---|---|---|---|
| 1.19 | 2-OCH₃ | H | −N(C₃H₇(n))(CH₂−CH₂−CN) | m.p. 89–91° |
| 1.20 | 2-Cl | 3-Cl | −N(C₃H₇(n))(CH₂−CH₂−CN) | semi-crystalline |
| 1.21 | 2-Cl | 3-Cl | −N(C₄H₉(n))(CH₂CH₂−CN) | semi-crystalline |
| 1.22 | 2-Cl | 3-Cl | −N(C₆H₁₃(n))(CH₂CH₂CN) | m.p. 48–49° |
| 1.23 | 2-Cl | 3-Cl | −N(CH(CH₃)₂)(CH₂−CH₂−CN) | m.p. 104–106° |
| 1.24 | 2-Cl | H | −N(CH(CH₃)₂)(CH₂−CH₂−CN) | m.p. 68–69° |
| 1.25 | 2-Cl | 3-Cl | −N(CH(CH₃)(CH₂CH₃))(CH₂−CH₂−CN) | m.p. 81–82° |
| 1.26 | 2-Cl | 3-Cl | −N(C(CH₃)₃)(CH₂−CH₂CN) | |
| 1.27 | 2-Cl | H | −N(C(CH₃)₃)(CH₂−CH₂−CN) | |
| 1.28 | H | H | −N(cyclopentyl-H)(CH₂CH₂CN) | |
| 1.29 | 2-Cl | 3-Cl | −N(cyclopentyl-H)(CH₂CH₂CN) | m.p. 70–71° |
| 1.30 | 2-Cl | 3-Cl | −N(cyclohexyl-H)(CH₂−CH₂CN) | |
| 1.31 | 2-OCH₃ | H | −N(cyclohexyl-H)(CH₂−CH₂CN) | |
| 1.32 | 2-Cl | 3-Cl | −N(CH₂−phenyl)(CH₂CH₂−CN) | m.p. 104–106° |
| 1.33 | H | H | −N(CH₂−phenyl-Cl)(CH₂CH₂−CN) | m.p. 89–91° |
| 1.34 | 2-Cl | 3-Cl | −N(CH₂CH₂OCH₃)(CH₂CH₂CN) | m.p. 73–75° |
| 1.35 | 2-Cl | H | −N(CH₂CH₂OCH₃)(CH₂CH₂CN) | m.p. 50–52° |
| 1.36 | 2-Cl | 3-Cl | −N(CH₂−phenyl)(cyclohexyl-H) | resin |
| 1.37 | 2-Cl | 3-Cl | −N(CH₂−phenyl-Cl)(CH₂CH₂CN) | m.p. 119–120° |

TABLE 1-continued
Compound of the formula
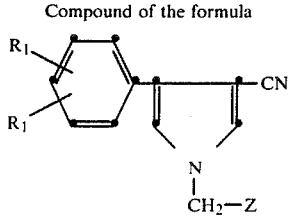
| Compound | R₁ | R₂ | Z | Physical data [°C.] |
|---|---|---|---|---|
| 1.38 | H | 3-Cl | 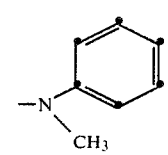 | |
| 1.39 | H | H | 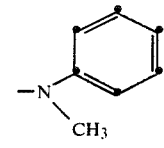 | |
| 1.40 | 2-Cl | 3-Cl | 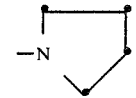 | |
| 1.41 | 2-Cl | H | 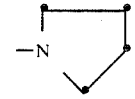 | |
| 1.42 | 2-Cl | 3-Cl | 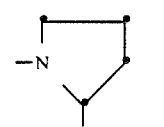 | m.p. 57–59° |
| 1.43 | 2-Cl | 3-Cl | 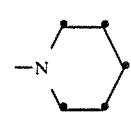 | |
| 1.44 | H | H | 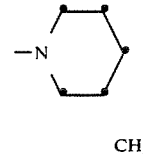 | |
| 1.45 | 2-Cl | 3-Cl | 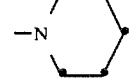 | m.p. 94–96° |
| 1.46 | 2-Cl | H | 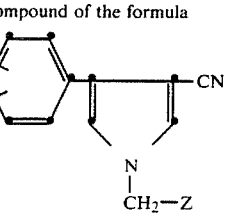 | |
| 1.47 | 2-Cl | 3-Cl | 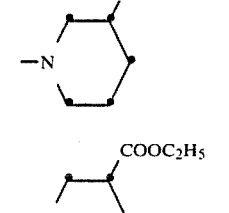 | |
| 1.48 | 2-Cl | H | 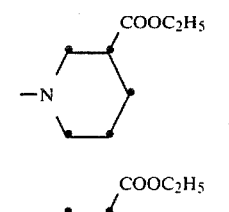 | $n_D^{50}$: 1.5571 |
| 1.49 | 2-Cl | 3-Cl | 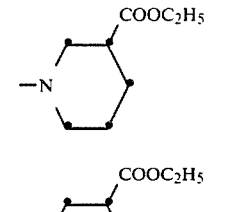 | |
| 1.50 | 2-OCH₃ | H | 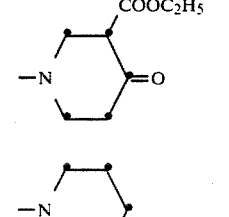 | resin |
| 1.51 | H | H | 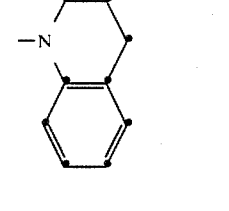 | |
| 1.52 | 2-SCH₃ | H | 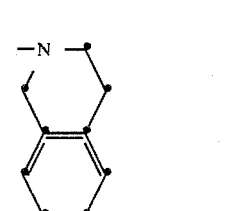 | |
| 1.53 | H | 3-Cl | 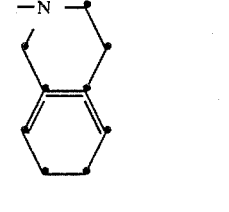 | |
| 1.54 | H | 3-Cl | 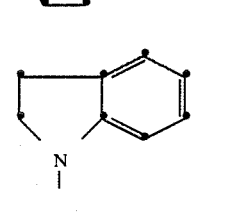 | |

TABLE 1-continued

Compound of the formula (structure: R₁, R₁ substituted phenyl—CH=C(CN)— pyrrole with N—CH₂—Z)

| Compound | R₁ | R₂ | Z | Physical data [°C.] |
|---|---|---|---|---|
| 1.55 | 2-Cl | 3-Cl | —N(morpholino, O) | m.p. 95–97° |
| 1.56 | 2-Cl | H | —N(morpholino, O) | m.p. 81–82° |
| 1.57 | H | H | —N(morpholino, O) | |
| 1.58 | 2-Cl | 3-Cl | —N(thiomorpholino, S) | |
| 1.59 | H | H | —N(2-methylmorpholino, CH₃, O) | |
| 1.60 | 2-Cl | 3-Cl | —N(2-methylmorpholino, CH₃, O) | |
| 1.61 | 2-Cl | H | —N(2,6-dimethylmorpholino, CH₃⁽¹⁾, O, CH₃) | m.p. 120–131° |
| 1.62 | H | 3-Cl | —N(2,6-dimethylmorpholino, CH₃⁽¹⁾, O, CH₃) | oil |
| 1.63 | 2-Cl | 3-Cl | —N(2,6-dimethylmorpholino, CH₃⁽¹⁾, O, CH₃) | m.p. 91–97° |
| 1.64 | 2-SCH₃ | H | —N(piperazino, N—CH₃) | |
| 1.65 | 2-Cl | H | —N(piperazino, N—CHO) | |
| 1.66 | 2-Cl | 3-Cl | —N(piperazino, N—CHO) | |
| 1.67 | H | H | —N(piperazino, N—CO—CH₃) | semi-crystalline |
| 1.68 | 2-Cl | 3-Cl | —N(piperazino, N—CO—CH₃) | m.p. 170–173° |
| 1.69 | H | 3-Cl | —N(piperazino, N—COOC₂H₅) | |
| 1.70 | 2-Cl | 3-Cl | —N(CH₃)(CH₂—CH=CH₂) | resin |
| 1.71 | H | H | —N(CH₂—CH=CH₂)₂ | |
| 1.72 | 2-Cl | 3-Cl | —N(CH₂—C≡CH)(cyclohexyl) | resin |
| 1.73 | 2-Cl | 3-Cl | —N(CH₂CH₃)(CH₂CH₂CN) | |
| 1.74 | 2-Cl | 3-Cl | —N(C₆H₁₃(n))(CH₂CH₂CN) | |

TABLE 1-continued

Compound of the formula

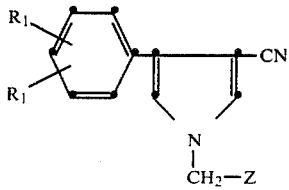

| Compound | R₁ | R₂ | Z | Physical data [°C.] |
|---|---|---|---|---|
| 1.75 | 2-Cl | 3-Cl | ![structure] | m.p. 102–104° |
| 1.76 | 2-Cl | 3-Cl | —N(CH₂CH₂CN)₂ | m.p. 142–144° |
| 1.77 | 2-Cl | 3-Cl | —N(CH₃)(CH₂COOCH₂CH₃) | |

$^{(1)}$mixtures of cis + trans isomers
$^{(2)}$pure isomer

FORMULATION EXAMPLES

Formulation Examples for liquid active ingredients of the formula I (throughout, percentages are by weight)

| F1. Emulsifiable concentrates | (a) | (b) | (c) |
|---|---|---|---|
| a compound of table 1 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| F2. Solutions | (a) | (b) | (c) | (d) |
|---|---|---|---|---|
| a compound of table 1 | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum distillate (boiling range 160–190°) | — | — | 94% | — |

These solutions are suitable for application in the form of microdrops.

| F3. Granulates | (a) | (b) |
|---|---|---|
| a compound of table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| F4. Dusts | (a) | (b) |
|---|---|---|
| a compound of table 1 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Formulation examples for solid active ingredients of the formula I (throughout, percentages are by weight)

| F5. Wettable powders | (a) | (b) | (c) |
|---|---|---|---|
| a compound of table 1 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixtures is thoroughly ground in a suitable mill, affording wettable powders which can be diluted with water to give suspensions of the desired concentration.

| F6. Emulsifiable concentrate | |
|---|---|
| a compound of table 1 | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| F7. Dusts | (a) | (b) |
|---|---|---|
| a compound of table 1 | 5% | 8% |
| talcum | 95% | — |
| kaolin | — | 92% |

Ready-for-use dusts are obtained by mixing the active ingredient with the carriers, and grinding the mixture in a suitable mill.

| F8. Extruder granulate | |
|---|---|
| a compound of table 1 | 10% |
| sodium lignosulfonate | 2% |
| carboxymethylcellulose | 1% |
| koalin | 87% |

The active ingredient is mixed and ground with the adjuvants, and the mixture is subsequently moistened with water. The mixture is extruded and then dried in a strem of air.

| F9. Coated granulate | |
|---|---|
| a compound of table 1 | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| F10. Suspension concentrate | |
|---|---|
| a compound of table 1 | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the aduvants, giving a suspension concentrate from which suspensions of any desired concentration can be obtained by dilution with water.

BIOLOGICAL EXAMPLES

EXAMPLE B1: Action against *Puccinia graminis* on wheat (a) Residual-protective action Wheat plants were treated 6 days after sowing with a spray mixture prepared from a wettable powder formulation of the test compound (0.06%). After 24 hours the treated plants were infected with a uredospore suspension of the fungus. The infected plants were incubated for 48 hours at 95-100% relative humidity and about 20° C. and then stood in a greenhouse at about 22° C. Evaluation of rust pustule development was made 12 days after infection.

(b) Systemic action

Wheat plants were treated 5 days after sowing with a spray mixture prepared from a wettable powder formulation of the test compound (0.006% based on the volume of the soil). After 48 hours the treated plants were infected with a uredospore suspension of the fungus. The plants were then incubated for 48 hours at 95-100% relative humidity and about 20° C. and then stood in a greenhouse at about 22° C. Evaluation or rust pustule development was made 12 days after infection.

Compounds of Table 1 were very effective against Puccinia fungi not only in the above greenhouse test but also in field trials. Puccinia attack was 100% on untreated and infected control plants. Compounds 1.11, 1.14, 1.15, 1.20, 1.21, 1.22, 1.23, 1.24, 1.28, 1.29, 1.33, 1.36, 1.37, 1.50, 1.72 and others inhibited Puccinia attack to 0 to 10%.

EXAMPLE B2: Action against *Cercospora arachidicola* in groundnut plants

Residual protective action

Groundnut plants 10-15 cm in height were sprayed with a spray mixture (0.006%) prepared from a wettable powder formulation of the test compound, and infected 48 hours later with a conidia suspension of the fungus. The infected plants were incubated for 72 hours at about 21° C. and high humidity and then stood in a greenhouse until the typical leaf specks occur. Evaluation of the fungicidal action was made 12 days after infection and was based on the number and size of the specks.

(b) Systemic action

Groundnut plants 10-15 cm in height were sprayed with a spray mixture prepared from a wettable powder formulation of the test compound (0.06%, based on the volume of the soil). The treated plants were infected 48 hours later with a conidia suspension of the fungus and then incubated for 72 hours at about 21° C. and high humidity. The plants were then stood in a greenhouse and evaluation of fungus attack was made 11 days later.

Compared with untreated and infected control plants (number and size of the specks=100%), Cercospora attack on groundnut plants treated in the greenhouse or in the field with compounds of Table 1 was substantially reduced. Thus compounds 1.9, 1.20, 1.21, 1.22, 1.23, 1.45, 1.55, 1.56, 1.63 and 1.68 inhibted the occurrence of specks almost completely (8%) in the above tests.

EXAMPLE B3: Action against *Botrytis cinerea* on beans

Residual protective action

Bean plants about 10 cm in height were sprayed with a spray mixture (0.02%) prepared from a wettable powder formulation of the test compound. After 48 hours the treated plants were infected with a conidia suspension of the fungus. The infected plants were incubated for 3 days at 95-100% relative humidity and 21° C. and then evaluated for fungus attack. The compounds of Table 1 inhibited the fungus infection very strongly not only in the above model test but also in field trials. At a concentration of 0.02%, compounds 1.1 1.2, 1.3, 1.9, 1.11, 1.14, 1.15, 1.16, 1.19 bis 1.25, 1.29, 1.32 to 1.37, 1.42, 1.45, 1.48, 1.50, 1.55, 1.56, 1.61, 1.63, 1.68, 1.70, 1.72, 1.75 and 1.76 were fully effective (0 to 5% attack). This activity was achieved with some representatives at half the rate of application. Fungus attack was 100% on untreated and infected bean plants. The intermediates 16 and 24 were equally effective.

EXAMPLE B4: Action against *Botrytis cinerea* on apples

Artificially damaged apples were treated by dropping a spray mixture prepared from the respective test compound formulated as wettable powder onto the injury sites. The treated fruit was then inoculated with a spore suspension of Botrytis cinerea and incubated for 1 week at high humidity and about 20° C. Evaluation was made by counting the number of injury sites attacked by rot and deducing the fungicidal action of the test compound therefrom. Compared with untreated controls (100% attack), compounds 1.1, 1.2, 1.3, 1.9, 1.11, 1.14, 1.15, 1.16, 1.19 bis 1.25, 1.29, 1.32 to 1.37, 1.42, 1.45, 1.48, 1.50, 1.55, 1.56, 1.61, 1.62, 1.63, 1.68, 1.70, 1.72, 1.75 and 1.76 and others inhibited fungus attack almost completely.

EXAMPLE B5: Action against Piricularia on rice plants

Residual protective action

After a cultivation period of 2 weeks, rice plants were sprayed with a spray mixture (0.02%) prepared from a wettable powder formulation of the test compound. After 48 hours the treated plants were infected with a conidia suspension of the fungus. Evaluation of fungus attack was made after incubation for 5 days at 95–100% relative humidity and 24° C. Compounds of formula I inhibited Piricularia attack effectively e.g. compounds 1.1, 1.16, 1.55, 1.61, 1.62 and 1.63. These compounds reduced attack to less than 10%.

EXAMPLE B6: Action against *Rhizoctonia solani* in cabbage

Action after soil application

The fungus was cultivated on sterile millet seeds and added to a mixture of soil and sand. Dishes were filled with the infected soil in which cabbage seeds were sown. Immediately after sowing, an aqueous suspension of the test compound formulated as wettable powder was poured onto the soil (20 ppm, based on the volume of the soil). The dishes were then put into a greenhouse for 2-3 weeks at about 24° C. and kept uniformly moist by light spraying. The test was evaluated by determining the number of emerged cabbage plants. After treatment with wettable powders which contained one of compounds 1.1, 1.61, 1.62 or 1.63 80% of the cabbage seeds emerged and the plants had a healthy appearance.

EXAMPLE B7: Residual-protective action against *Venturia inaequalis* on apple shoots Apple cuttings with 10–20 cm long fresh shoots were sprayed with a spray mixture (0.006%) prepared from a wettable powder formulation of the test compound. The plants were infected 24 hours later with a conidia suspension of the fungus. The plants were then incubated for 5 days at 90–100% relative humidity and stood in a greenhouse for a further 10 days at 20°–24° C. Evaluation of scab infestation was made 15 days after infection.

Compounds of formula I were very effective against Venturia pathogens. Compared with attack on untreated control plants, scab attack was inhibited to less than 20% with compounds 1.1, 1.9, 1.45, 1.55, 1.62 and 1.63.

EXAMPLE B8: Action against *Helminthosporium gramineum*

Wheat grains were contaminated with a spore suspension of the fungus and dried. The contaminated grains were dressed with a suspension of the test compound prepared from a wettable powder (600 ppm of test compound, based on the weight of the seeds). Two days later the grains were placed in suitable agar dishes and a count of the fungus colonies which had developed around the grains was made after another 4 days. The effectiveness of the test compounds was assessed on the basis of the number and size of the colonies. Compounds of Table 1 inhibited fungus attack substantially (0 to 10%).

EXAMPLE B9: Action against *Fusarium nivale*

Wheat grains were contaminated with a spore suspension of the fungus and dried. The contaminated grains were dressed with a suspension of the test compound prepared from a wettable powder (600 ppm of test compound, based on the weight of the seeds). Two days later the grains were placed in suitable agar dishes and a count of the fungus colonies which had developed around the grains was made after another 4 days. The effectiveness of the test compounds was assessed on the basis of the number and size of the colonies. The development of fungus colonies was almost completely inhibited (0 to 5%) on wheat grains treated with a wettable powder formulation of one of the compounds of Table 1.

EXAMPLE 10: Action against *Alternaria solani* on tomatoes

After a cultivation period of 3 weeks, tomato plants were sprayed with a spray mixture (0.006%) prepared from a wettable powder formulation of the test compound. After 24 hours the tomato plants were treated with a conidia suspension of the fungus. Evaluation of fungicidal action was made on the basis of fungus attack after the plants had been incubated for 8 days at high humidity and a temperature of 18°–22° C.

Not only in the above model test, but also under field conditions, compounds of Table 1 were very effective against Alternaria solani. Thus, for example, compounds 1.1, 1.2, 1.3, 1.9, 1.15, 1.16, 1.19, 1.22, 1.23, 1.24, 1.25, 1.29, 1.34, 1.35, 1.45, 1.48, 1.55, 1.56, 1.61, 1.62, 1.63, 1.68 and others reduced fungus attack to 0 to 10%, whereas fungus attack was 100% on untreated and infected control plants.

What is claimed:

1. A compound of the formula I

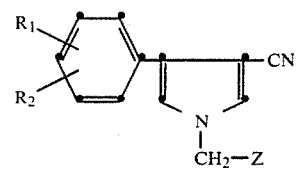

wherein
$R_1$ and $R_2$ are each independently hydrogen, halogen, methoxy or methylthio,
Z is a group

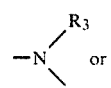

(a)

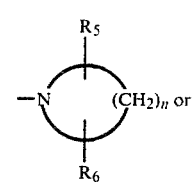

(b)

-continued $$\begin{array}{c} R_7 \\ | \\ -N \diagup\!\!\!\!\diagdown X \\ \diagdown\!\!\!\!\diagup \\ | \\ R_8 \end{array} \quad (c)$$

wherein
- $R_3$ and $R_4$ are each independently hydrogen, $C_1$-$C_6$alkyl which is unsubstituted or substituted by cyano, $C_1$-$C_6$alkoxy or $C_1$-$C_6$alkoxycarbonyl; or are $C_3$-$C_6$alkenyl, $C_3$-$C_6$alkynyl, $C_3$-$C_7$cycloalkyl, benzyl or benzyl which is substituted by halogen, $C_1$-$C_6$alkyl, $C_1$-$C_6$haloalkyl and/or $C_1$-$C_6$alkoxy, or phenyl or phenyl which is substituted by halogen, $C_1$-$C_6$alkyl, $C_1$-$C_6$haloalkyl and/or $C_1$-$C_6$alkoxy, with the proviso that only one of $R_3$ or $R_4$ may be hydrogen,
- $R_5$ and $R_6$ are each independently hydrogen, $C_1$-$C_6$alkyl, $C_1$-$C_6$alkoxycarbonyl, or both taken together form a fused aromatic ring,
- n is 4 or 5,
- X is oxygen, sulfur, $>C=O$ or $>N$-$R_9$
- $R_7$ and $R_8$ are each independently hydrogen, $C_1$-$C_6$alkyl or $C_1$-$C_6$alkoxycarbonyl, and
- $R_9$ is hydrogen, $C_1$-$C_6$alkyl, formyl, $C_1$-$C_6$alkanoyl or $C_1$-$C_6$alkoxycarbonyl.

2. A compound of the formula I according to claim 1, wherein $R_1$ and $R_2$ are each independently hydrogen, chlorine, methoxy or methylthio, Z is a group $$-N\diagup\!\!\!\!\diagup^{R_3}_{R_4} \quad \text{or} \quad (a)$$

$$\begin{array}{c} R_5 \\ | \\ -N \diagup\!\!\!\!\diagdown (CH_2)_n \\ \diagdown\!\!\!\!\diagup \\ | \\ R_6 \end{array} \quad \text{or} \quad (b)$$

$$\begin{array}{c} R_7 \\ | \\ -N \diagup\!\!\!\!\diagdown X \\ \diagdown\!\!\!\!\diagup \\ | \\ R_8 \end{array} \quad (c)$$

wherein $R_3$ and $R_4$ are each independently hydrogen, $C_1$-$C_6$alkyl, $C_1$-$C_3$alkyl which is substituted by cyano, $C_1$-$C_3$alkoxy or $C_1$-$C_3$alkoxycarbonyl; or are $C_3$-$C_4$alkenyl, $C_3$-$C_4$alkynyl, $C_5$-$C_6$cycloalkyl, benzyl or benzyl which is substituted by halogen, methyl, trifluoromethyl and/or methoxy, or phenyl or phenyl which is substituted by halogen, methyl, trifluoromethyl and/or methoxy, with the proviso that only one of $R_3$ or $R_4$ may be hydrogen; $R_5$ and $R_6$ are each independently hydrogen, $C_1$-$C_3$alkyl or $C_1$-$C_3$alkoxycarbonyl, or both taken together form a fused phenyl ring; n is 4 or 5, X is oxygen, sulfur, $>C=O$ or $>N$-$R_9$; $R_7$ and $R_8$ are each independently hydrogen, $C_1$-$C_3$alkyl or $C_1$-$C_3$alkoxycarbonyl; and $R_9$ is hydrogen, $C_1$-$C_3$alkyl, formyl, $C_1$-$C_3$alkanoyl or $C_1$-$C_3$alkoxycarbonyl.

3. A compound of the formula I according to claim 2, wherein $R_1$ is in the 2-position and $R_2$ is in the 3-position and each independently of the other is hydrogen, methoxy or methylthio; Z is a group $$-N\diagup\!\!\!\!\diagup^{R_3}_{R_4} \quad \text{or} \quad (a)$$

$$\begin{array}{c} R_5 \\ | \\ -N \diagup\!\!\!\!\diagdown (CH_2)_n \\ \diagdown\!\!\!\!\diagup \\ | \\ R_6 \end{array} \quad \text{or} \quad (b)$$

$$\begin{array}{c} R_7 \\ | \\ -N \diagup\!\!\!\!\diagdown X \\ \diagdown\!\!\!\!\diagup \\ | \\ R_8 \end{array} \quad (c)$$

wherein $R_3$ and $R_4$ are each independently $C_1$-$C_6$alkyl, $C_1$-$C_2$alkyl which is substituted by cyano, $C_1$-$C_3$alkoxy or $C_1$-$C_3$alkoxycarbonyl; or are allyl, propargyl, cyclopentyl, cyclohexyl, benzyl, halobenzyl, phenyl or halophenyl; $R_5$ and $R_6$ are each independently hydrogen, methyl or $C_1$-$C_3$alkoxycarbonyl, or both taken together form a fused phenyl ring; n is 4 or 5, X is oxygen, sulfur, $>C=O$ or $>N$-$R_9$ and $R_7$ and $R_8$ are each independently hydrogen, $C_1$-$C_3$alkyl or $C_1$-$C_3$alkoxycarbonyl, and $R_9$ is hydrogen, $C_1$-$C_3$alkyl, formyl, $C_1$-$C_3$alkanoyl or $C_1$-$C_3$alkoxycarbonyl.

4. A compound of the formula I according to claim 3, wherein $R_1$ is hydrogen or 2-chloro and $R_2$ is hydrogen or 3-chloro; Z is a group $$-N\diagup\!\!\!\!\diagup^{R_3}_{R_4} \quad \text{or} \quad (a)$$

$$\begin{array}{c} R_5 \\ | \\ -N \diagup\!\!\!\!\diagdown (CH_2)_n \\ \diagdown\!\!\!\!\diagup \\ | \\ R_6 \end{array} \quad \text{or} \quad (b)$$

$$\begin{array}{c} R_7 \\ | \\ -N \diagup\!\!\!\!\diagdown X \\ \diagdown\!\!\!\!\diagup \\ | \\ R_8 \end{array} \quad (c)$$

wherein $R_3$ and $R_4$ are each independently $C_1$-$C_6$alkyl, $C_1$-$C_2$alkyl which is substituted by $C_1$-$C_3$alkoxy or $C_1$-$C_3$alkoxycarbonyl; or are allyl, propargyl, cyclopentyl, cyclohexyl, benzyl, halobenzyl, phenyl or halophenyl; $R_5$ and $R_6$ are each independently hydrogen, methyl or $C_1$-$C_3$alkoxycarbonyl, or both taken together form a fused phenyl ring; n is 4 or 5, X is oxygen, sulfur, $>C=O$ or $>N$-$R_9$; and $R_7$ and $R_8$ are each independently hydrogen, methyl or $C_1$–$C_3$alkoxycarbonyl, and $R_9$ is hydrogen, $C_1$–$C_2$alkyl, formyl, $C_1$–$C_3$alkanoyl or $C_1$–$C_3$alkoxycarbonyl.

5. A compound of the formula I according to claim 1, selected from the group consisting of N-(N',N'-dimethylaminomethyl)-3-(2,3-dichlorophenyl)-4-cyanopyrrole, N-(N'-benzyl-N'-methylaminomethyl)-3-(2,3-dichlorophenyl)-4-cyanopyrrole, N-[N'-methyl-N'-(2-cyanoethyl)aminomethyl]-3-(2,3-dichlorophenyl)-4-cyanopyrrole, N-[N'-isopropyl-N'-(2-cyanoethyl)aminomethyl]-3-(2,3-dichlorophenyl)-4-cyanopyrrole, N-(piperidin-1-ylmethyl)-3-(2,3-dichlorophenyl)-4-cyanopyrrole, N-(3-ethoxycarbonylpiperidin-1-ylmethyl)-3-(2-chlorophenyl)-4-cyanopyrrole, N-(morpholin-1-ylmethyl)-3-(2,3-dichlorophenyl)-4-cyanopyrrole, N-(2,6-dimethylmorpholin-1-ylmethyl)-3-(2-chlorophenyl)-4-cyanopyrrole, N-[N'-cyclopentyl-N'-(2-cyanoethyl)aminomethyl]-3-(2,3-dichlorophenyl)-4-cyanopyrrole, N-(2,6-dimethylmorpholin-1-ylmethyl)-3-(2,3-dichlorophenyl)-4-cyanopyrrole, N-(4-acetylcarbonylpiperazin-1-ylmethyl)-3-(2,3-dichlorophenyl)-4-cyanopyrrole, N-[N'-2-(methoxyethyl)-N'-(2-cyanoethyl)aminomethyl]-3-(2,3-dichlorophenyl)-4-cyanopyrrole, N-[N'-methyl-N'-(2-cyanoethyl)aminomethyl]-3-(2-chlorophenyl)-4-cyanopyrrole, N-[N'-methyl-N'-(2-methoxyethyl)aminomethyl]-3-(2,3-dichlorophenyl)-4-cyanopyrrole, N-[N'-(n-propyl)-N'-(2-cyanoethyl)aminomethyl]-3-(2,3-dichlorophenyl)-4-cyanopyrrole, N-[N'-(n-butyl)-N'-(2-cyanoethyl)aminomethyl]-3-(2,3-dichlorophenyl)-4-cyanopyrrole, N-[N'-methyl-N'-prop-2-enyl-aminomethyl]-3-(2,3-dichlorophenyl)-4-cyanopyrrole, and N-[N'-propargyl-N'-cyclohexylaminomethyl]-3-(2,3-dichlorophenyl)-4-cyanopyrrole.

6. The compound according to claim 5 which is N-(N')N'-dimethylaminomethyl)-3-(2,3-dichlorophenyl)-4-cyanopyrrole.

7. A microbicidal composition for controlling phytopathogenic microorganisms or for protecting living plants from attack by such microorganisms and/or for preserving perishable storable goods of vegetable or animal origin, which composition contains at least one compound of the formula I according to claim 1 and a carrier.

8. A method of controlling phytopathogenic microorganisms or of protecting cultivated plants from attack by said microorganisms, which method comprses applying to said plants, to part of plants or to the locus thereof a microbicidally effective amount of a compound of the formula I according to claim 1 and a carrier.

9. A method of preserving or protecting storable goods which comprises spraying or wetting said goods with a liquid formulation or mixing said goods with a solid formulation containing a microboicidally effective amount of a compound of the formula I according to claim 1.

* * * * *